(12) United States Patent
Li (10) Patent No.: US 11,534,840 B2
(45) Date of Patent: *Dec. 27, 2022

(54) DEPTH LIMITING DEVICE

(71) Applicant: Kai Li, Taiyuan (CN)

(72) Inventor: Kai Li, Taiyuan (CN)

(*) Notice: Subject to any disclaimer, the term of this patent is extended or adjusted under 35 U.S.C. 154(b) by 110 days.

This patent is subject to a terminal disclaimer.

(21) Appl. No.: 17/060,246

(22) Filed: Oct. 1, 2020

(65) Prior Publication Data

US 2021/0016369 A1 Jan. 21, 2021

Related U.S. Application Data

(63) Continuation of application No. 16/213,076, filed on Dec. 7, 2018, now Pat. No. 10,814,404, which is a
(Continued)

(51) Int. Cl.
*B23B 49/00* (2006.01)
*A61B 17/16* (2006.01)
(Continued)

(52) U.S. Cl.
CPC ........ *B23B 49/006* (2013.01); *A61B 17/1633* (2013.01); *A61B 90/03* (2016.02);
(Continued)

(58) Field of Classification Search
CPC ... B23B 49/003; B23B 49/006; B23B 49/005; B23B 45/003; B23B 49/008; B23B 2260/048; B23B 2260/0482; B23B 2260/0485; B23B 2260/0487; B23B 2260/12; B23B 2260/136; B25F 5/003; Y10T 408/99; Y10T 408/8925;
(Continued)

(56) References Cited

U.S. PATENT DOCUMENTS 4,207,953 A 6/1980 Reibetanz et al.
4,281,949 A 8/1981 Bugarin
(Continued)

FOREIGN PATENT DOCUMENTS

DE 3800482 A1 7/1989
DE 3801141 A1 7/1989
(Continued)

OTHER PUBLICATIONS

Machine Translation, KR 2009-0115395 A. (Year: 2009).*
Machine Translation, DE3801141 (A1). (Year: 1989).*

*Primary Examiner* — Chwen-Wei Su
(74) *Attorney, Agent, or Firm* — SZDC Law P.C.

(57) ABSTRACT

A depth limiting device includes a braking structure; a limited shrinking structure, the limited shrinking structure including a part that surrounds a moving object and being in a home position or a compressed position; and a structure adapted for pushing the limited shrinking structure to the home position. The braking structure brakes the moving object such that the moving object moves together with the depth limiting device. When the moving object enters into a subject, the part of the limited shrinking structure is pressed against the subject, and the limited shrinking structure moves from the home position to the compressed position and stops the moving object from entering further into the subject.

5 Claims, 9 Drawing Sheets

Related U.S. Application Data continuation of application No. 15/384,539, filed on Dec. 20, 2016, now Pat. No. 10,183,339.

(51) Int. Cl.
 *A61B 90/00* (2016.01)
 *B25F 5/00* (2006.01)
(52) U.S. Cl.
 CPC ...... *B23B 49/005* (2013.01); *A61B 2090/033* (2016.02); *A61B 2090/036* (2016.02); *B23B 2260/136* (2013.01); *B25F 5/003* (2013.01); *Y10T 408/18* (2015.01); *Y10T 408/8925* (2015.01); *Y10T 408/99* (2015.01)
(58) Field of Classification Search
 CPC . Y10T 408/18; Y10T 408/8928; A61B 90/03; A61B 2090/036; A61B 2090/066; A61B 2090/033; A61B 17/1633; A61B 17/1695; A61B 17/17; A61B 2017/00991; A61B 2090/003

See application file for complete search history.

(56) References Cited

U.S. PATENT DOCUMENTS

| | | | |
|---|---|---|---|
| 5,071,293 A | * | 12/1991 | Wells .................... B23Q 5/263 408/112 |
| 5,252,010 A | | 10/1993 | Obrecht et al. |
| 2009/0318927 A1 | | 12/2009 | Martin |
| 2016/0120553 A1 | | 5/2016 | Xie |
| 2017/0181758 A1 | | 6/2017 | Brotman |

FOREIGN PATENT DOCUMENTS

| | | |
|---|---|---|
| DE | 102013209677 A1 | 11/2014 |
| KR | 2009115395 A * | 11/2009 |

* cited by examiner

DEPTH LIMITING DEVICE

This application is a Continuation Application of U.S. patent application Ser. No. 16/213,076, filed on Dec. 7, 2018, which is a Continuation Application of U.S. patent application Ser. No. 15/384,539, filed on Dec. 20, 2016, now U.S. Pat. No. 10,183,339, issued on Jan. 22, 2019.

BACKGROUND OF THE INVENTION

Field of the Invention

The present invention relates to a depth limiting device.

Discussion of the Related Art

A drill is a tool used for drilling a hole in a subject. For example, a bone drill can be used for drilling a hole in a bone in a surgery. When a drill is used for drilling a hole in a bone, a surgical doctor holds the drill and pressurizes for drilling. After the drill breaks through the bone substance completely, the electric drill falls through, and it is often difficult and even sometime impossible for the surgical doctor to stop pressurizing at the same time, so the drill may drill forwards continuously. In the drilling process, damages of tissues may be resulted; and if vessels and nerves existing in the heading direction of the drill are damaged, serious consequences may be resulted. In addition, measurement of the depth of the drilling hole is also needed for determination of a suitable screw after the hole drilling process is finished. Existing drills, however, only have a hole drilling function, so the surgical doctor needs to measure the drilling hole by inserting a depth measuring device in the drilled hole. There is a need for improved drill that will reduce the damages to tissues, vessels, and nerves during the drilling process.

SUMMARY OF THE INVENTION

According to one embodiment, there is provided a depth limiting device for a drill that includes a main body; an axial braking structure, the axial braking structure being attached to the main body; and a limited shrinking structure, the limited shrinking structure surrounding a drill rod of the drill, being slidably attached to the main body, and being in a home position or a compressed position. The axial braking structure axially brakes the drill rod such that the drill rod moves together with the depth limiting device. When the drill rod enters into a subject, the limited shrinking structure is pressed against the subject, moves from the home position to the compressed position, and stops the drill rod from entering further into the subject.

In another embodiment, the limited shrinking structure includes a connecting sleeve, a drill rod bushing, and a first spring; the drill rod bushing houses the drill rod and slides relative to the drill rod; the connecting sleeve includes a retraction space therein and the first spring is located in the retraction space.

In another embodiment, the axial braking structure comprises a plurality of grooves adapted for axially braking the drill rod, a structure with a bulge which can be clamped in each groove, and an operating part for the structure with the bulge.

In another embodiment, the axial braking structure further includes an axial braking block and a second spring. A hole is formed in the axial braking block, the structure with the bulge is formed at an inner wall of the hole, the drill rod passes through the hole, the plurality of grooves are formed on the drill rod, the axial braking block is located inside the main body, the axial braking block has a compression fitting surface adapted for lifting the axial braking block and an opposite side of the compression fitting surface, and a cavity is formed between the opposite side and the main body. The second spring is located in the cavity.

In another embodiment, the axial braking structure further includes a trigger, a limiting rod, and a third spring. The trigger includes a hand-held section and a horizontal section, the horizontal section is vertical to the hand-held section, the horizontal section of the trigger is vertical to the axial braking block, a front end of the horizontal section of the trigger connects with the compression fitting surface. The limiting rod connects with one end of the horizontal section of the trigger and the compression fitting surface. The third spring is located between another end of the horizontal section of the trigger and the main body, and the another end of the horizontal section of the trigger is supported at the main body.

In another embodiment, the main body includes a handle and a protective plate. The protective plate connects with the handle and protecting the trigger.

In another embodiment, the main body further includes a front part and a rear part. The rear part surrounds the axial braking block, the front part supports the trigger, the connecting sleeve and the first spring are located inside the rear part, a front end of the drill rod bushing is attached to the front part, and a rear end of the drill rod bushing is slidably attached to the connecting sleeve.

In another embodiment, the axial braking structure includes a friction braking structure for the drill rod and an operating part for the friction braking structure.

In another embodiment, the friction braking structure includes an outer taper sleeve, an inner taper sleeve, a sixth spring, a trigger, and a U-shaped connecting rod. The outer taper sleeve surrounds the drill rod, the inner taper sleeve surrounds the outer taper sleeve and is attached inside the main body, an outer surface of the outer taper sleeve and an inner surface of the inner taper sleeve are in a friction fit, an expansion space is formed inside the inner taper sleeve, the sixth spring is located in the expansion space, a bottom of the U-shaped connecting rod connects with the trigger, two ends of the U-shaped connecting rod connects with two rollers, and the two rollers drive the outer taper sleeve towards the inner taper sleeve along the drill rod.

In another embodiment, the depth limiting device further includes a handle. The handle is parallel to the trigger and attached to the rear end of the main body, and the connecting sleeve is attached to the front end of the main body.

In another embodiment, the main body includes a protective sleeve, a sheath, a sleeve cylinder, and a seventh spring. The protective sleeve surrounds the drill rod, the sheath surrounds the protective sleeve, the sleeve cylinder is attached to drill rod, a rear end of the sheath connects with a front end of the sleeve cylinder, a rear end of the protective sleeve is located inside the sheath and slidably connects with the sheath, a front end of the protective sleeve connects with the connecting sleeve, and the seventh spring is located between the connecting sleeve and the sheath.

In another embodiment, the depth limiting device further includes a guide block and a limiting pin. The rear end of the protective sleeve protects the guide block which can slide along the inner wall of the sheath, and the limiting pin is located on the rear end of the sheath and brakes the guide block.

In another embodiment, the depth limiting device further includes a braking ring, a second connecting rod, and a trigger. The braking ring is located on the protective sleeve and within the sheath, the braking ring connects with the trigger via the second connecting rod, gaps exist between the inner wall of the breaking ring and the outer wall of the protective sleeve and between the outer wall of the braking ring and the inner wall of the sheath, a wall thickness center of the braking ring is coincided with a center of a gap between the protective sleeve and the sheath, and a rear end of the second connecting rod is supported at the main body.

In another embodiment, the depth limiting device further includes a second locking block, a steel sheet spring, a trigger, and a third connecting rod. The second lock block is rotationally attached to the sheath, the steel sheet spring is adapted for returning the second locking block to an original position, one end of the second locking block touches the periphery of a back section of the protective sleeve, another end of the second locking block connects with the trigger through the third connecting rod, and a rear end of the third connecting rod is supported at the main body.

In another embodiment, a drill includes the depth limiting device described above.

In yet another embodiment, there is provided a depth limiting device for a drill. The depth limiting device includes a main body; a locking shaft, the locking shaft having a plurality of grooves; a first locking block, one end of the first locking block having a bulge; a linear motion cam, the linear motion cam connecting with another end of the first blocking block; a rotary motion cam, the rotary motion cam connecting with the linear motion cam; a guide sleeve, the guide sleeve being located at outside of the first locking block, a retraction space being formed between the guide sleeve and the linear motion cam, and a forth spring being located in the retraction space; a first connecting rod, an end of the first connecting rod connecting with a drill rod of the drill; and a connecting sleeve, the connecting sleeve being located at a front end of the locking shaft and slidably connecting with another end of the first connecting rod. A rear end of the locking shaft and the main body form an expansion space, and a fifth spring is located in the expansion space.

In another embodiment, the main body is attached to a drill via a bracket.

In another embodiment, a drill includes the depth limiting device described above.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

In the Figures, the reference numerals have the followings designations:

1—drill rod, 2—drill rod bushing, 3—connecting sleeve, 4—retraction space, 5—first spring, 6—axial braking block, 7—cavity, 8—second spring, 9—trigger, 9.1—hand-held section, 9.2—horizontal section, 10—compression fitting surface, 11—limiting rod, 12—third spring, 13—handle, 14—protective plate, 15—main body, 15.1—front part, 15.2—rear part, 16—locking shaft, 17—first locking block, 18—linear motion cam, 19—rotary motion cam, 20—guide sleeve, 21—forth spring, 22—first connecting rod, 23—fifth spring, 24—bracket, 25—electric drill, 26—outer taper sleeve, 27—inner taper sleeve, 28—sixth spring, 29—U-shaped connecting rod, 30—roller, 31—protective sleeve, 32—sheath, 33—sleeve cylinder, 34—guide block, 35—limiting pin, 36—braking ring, 37—second connecting rod, 38—second locking block, 39—third connecting rod, 40—seventh spring, 100—subject, 101—limited shrinking structure, and 102—axial braking structure.

DETAILED DESCRIPTION OF THE ILLUSTRATED EMBODIMENTS

The depth limiting device used for a drill of the present invention is further described in detail by combining with the accompanying drawings.

The depth limiting device used for a drill includes a main body; an axial braking structure, braking the drill rod axially at any time; and a limited shrinking structure capable of sliding relative to a drill rod of the drill, realizing limited extension of the drill rod. The axial braking structure is attached to the main body.

Figure 1:
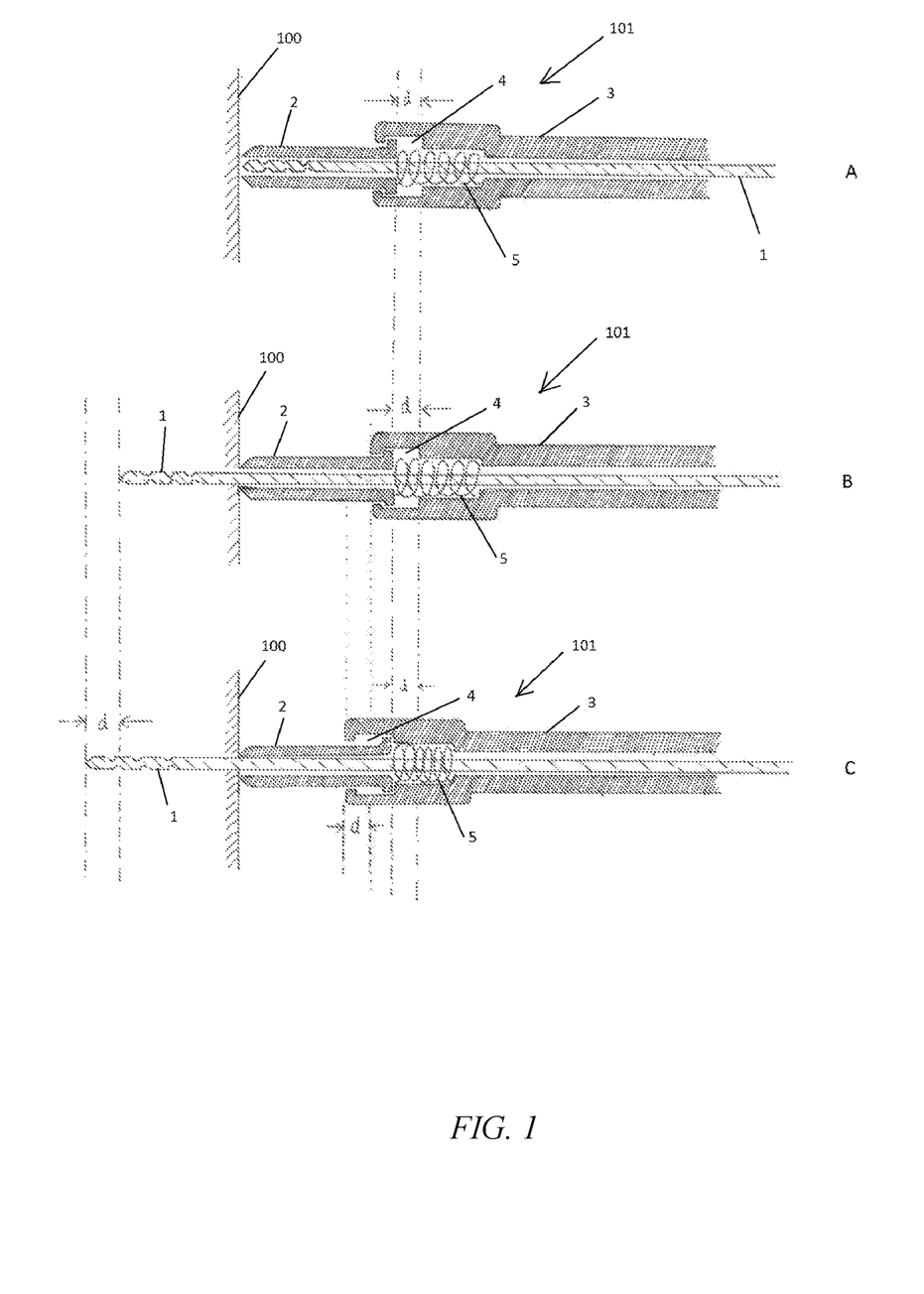
FIG. 1 shows a limited shrinking structure.

The limited shrinking structure surrounds a drill rod of the drill, is slidably attached to main body, and can be in a home position or a compressed position. FIG. 1A and FIG. 1B show a limited shrinking structure 101 in a home position where first spring 5 pushes drill rod bushing 2 forward against the front end of connecting sleeve 3. First spring 5 is located in retraction space 4. Other structures that have a same function as first spring 5 can be used instead of first spring 5. FIG. 1C shows that the limited shrinking structure 101 in a compressed position. Specifically, the axial braking structure axially brakes drill rod 1 such that the drill rod 1 moves together with the depth limiting device. When drill rod 1 enters into a subject 100, drill rod bushing 2 is pressed against the subject 100, moves from the home position to the compressed position, and stops the drill rod from entering further into the subject 100. Distance 'd' is the distance that drill rod bushing 2 moves from the home position to the compression, and it is also the depth limit of the depth limiting device. After the drilling is complete, first spring 5 pushes drill rod bushing 2 back to the home position.

The axial braking structure includes a plurality of groove structures capable of axially braking the drill rod, a structure with a bulge which can be clamped in each groove and an operating part of the structure. Alternatively, the axial braking structure includes a friction braking structure that results in friction braking for the drill rod and an operating part of the friction braking structure.

The depth limiting device is further illustrated in the following examples.

Figure 2:
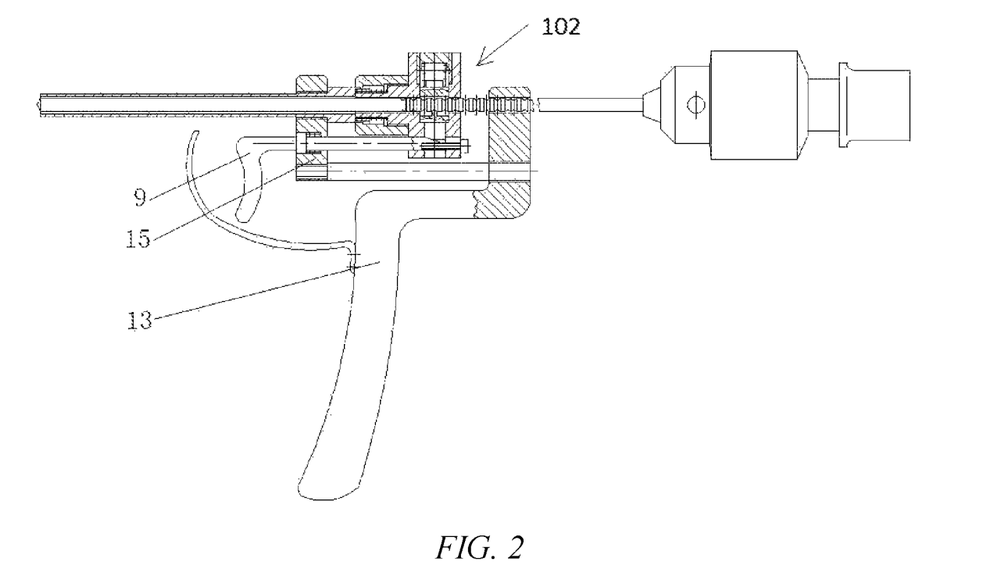
FIG. 2 is a side view of the depth limiting device of Example 1.
Figure 3:
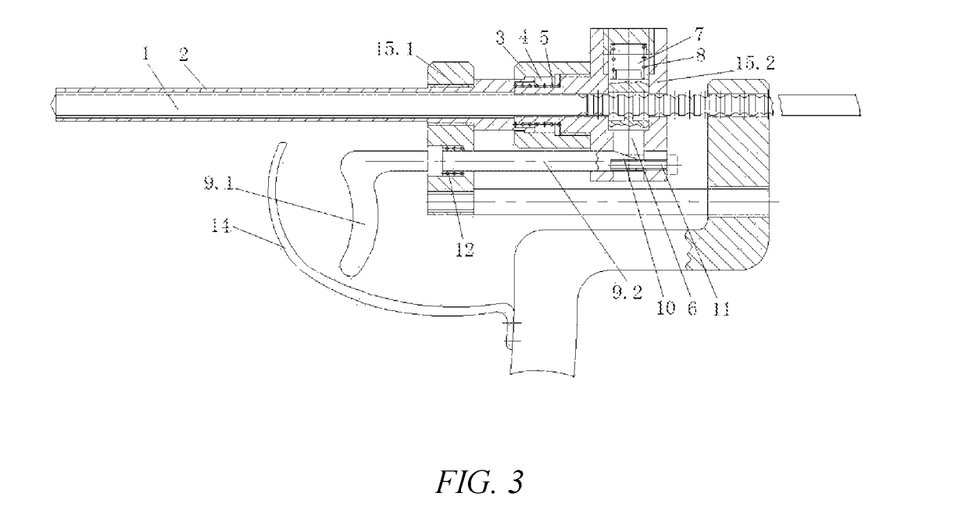
FIG. 3 is a partial enlarged drawing of FIG. 1.

Example 1: as shown in the FIGS. 2 and 3, axial braking structure 102 includes an axial braking block 6; a through hole that is formed in the axial braking block 6; a drill rod 1 with multiple grooves in the same shape that penetrates the through hole; and a bulge which can be clamped into each groove that is formed at the inner wall of the through hole. The axial braking block 6 is located in the main body 15, and has a compression fitting surface 10 adapted for lifting the axial braking block 6 and an opposite side of the compression fitting surface 10. A cavity 7 is formed between the opposite side and the main body 15, and a second spring (reset spring) 8 of the axial braking block 6 is arranged in the cavity 7. The axial braking structure further includes a trigger 9. The trigger 9 includes a hand-held section 9.1 and a horizontal section 9.2 which is vertical to the hand-held section 9.1; the horizontal section 9.2 of the trigger 9 is vertical to the axial braking block 6. The compression fitting surface 10 is arranged between the front end of the horizontal section 9.2 of the trigger 9 and the bottom of the axial braking block 6; the main body 15 is provided with a limiting rod 11 with the position thereof corresponding to one end of the horizontal section 9.2 of the trigger 9 where the compression fitting surface 10 is arranged; the other end of the horizontal section 9.2 of the trigger 9 is supported at the main body 15; and a third spring (reset spring) 12 is arranged between the other end of the horizontal section 9.2 of the trigger 9 and the main body 15. The main body 15 includes a front part 15.1 and a rear part 15.2; the rear part 15.2 is arranged outside the axial braking block 6; the trigger 9 is supported at the front part 15.1; the connecting sleeve 3 and the first spring 5 of the limited shrinking structure are arranged at the rear part 15.2; the drill rod bushing 2 which is arranged on the drill rod 1 in a sleeving manner is arranged at the front part 15.1 of the main body 15 in a penetrating manner and is fixedly connected with the front part 15.1; the end part of the rear end of the drill rod bushing 2 is connected in the connecting sleeve 3 in the sliding manner; retraction space 4 of the drill rod bushing 2 remains in the connecting sleeve 3, and the first spring 5 is arranged in the retraction space 4.

Figure 4:
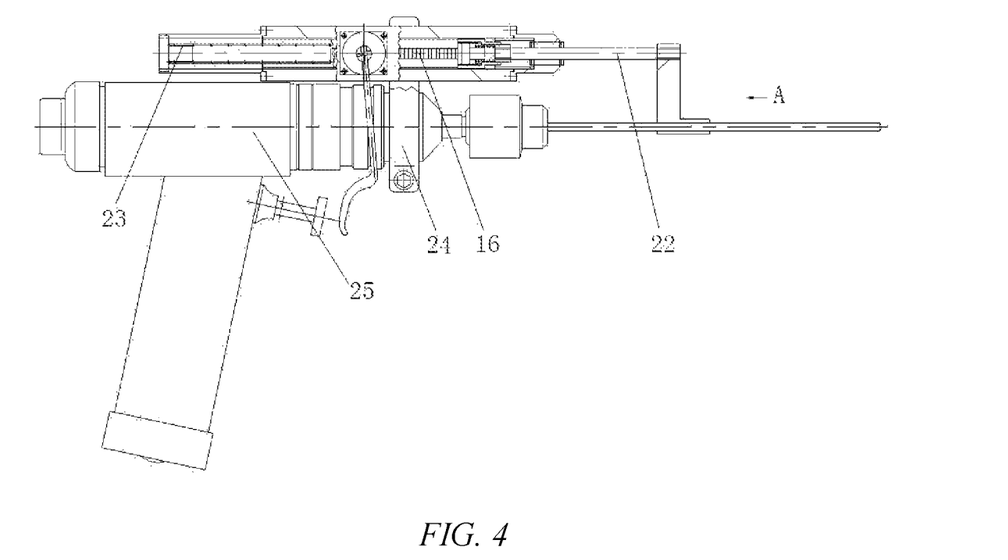
FIG. 4 is a side view of the depth limiting device of Example 2.
Figure 5:
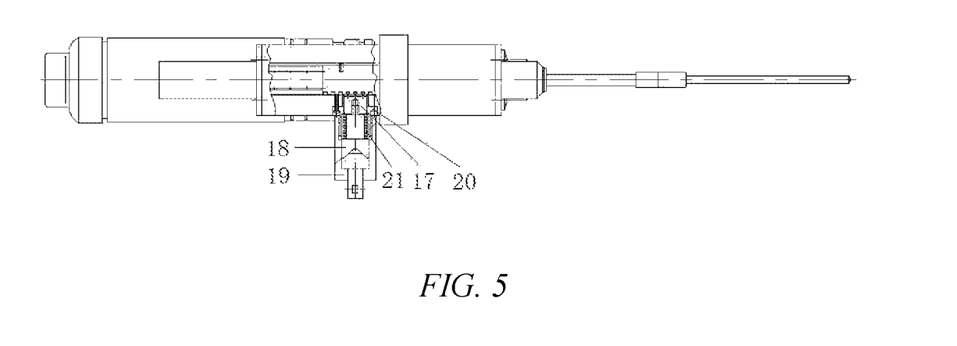
FIG. 5 is a top view of the depth limiting device shown in FIG. 3.
Figure 6:
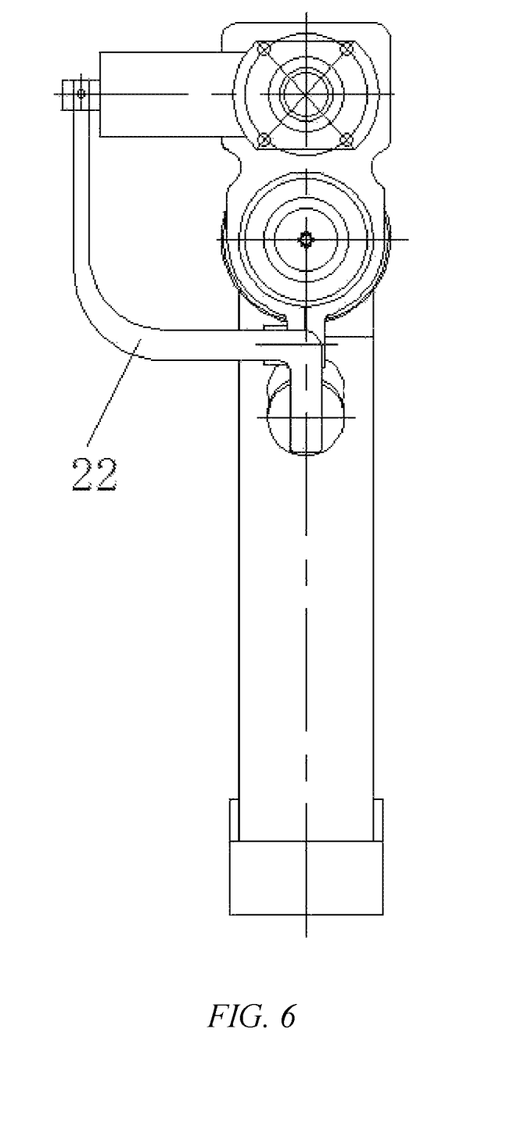
FIG. 6 is a cross-sectional view taken through A in FIG. 3.

Example 2: as shown in the FIGS. 4, 5 and 6, the axial braking structure includes a locking shaft 16, the groove structures being formed in the locking shaft; a structure with a bulge which can be clamped in each groove, the structure being a first locking block 17, the bulge being arranged at one end of the first locking block while the other end of the first locking block is connected with a linear motion cam 18; a rotary motion cam 19 which matches the linear motion cam is connected with a trigger; a guide sleeve 20 which is located at the outside of the first locking block is arranged at the position corresponding to the first locking block of the main body; expansion space of the first locking block being arranged between the guide sleeve and a cam base; a spring 21 being arranged in the expansion space; the main body corresponding to the front end of the locking shaft is provided with a connecting sleeve 3; a first connecting rod 22 being connected in the connecting sleeve 3 in the sliding manner; the connecting sleeve 3 internally including retraction space 4 of the first connecting rod; a spring 23 being arranged in the retraction space; the other end of the connecting rod being arranged at the outside of the drilling rod in a sleeving manner to form the drilling rod bushing; expansion space existing between the rear end of the locking shaft and the main body; and a fifth spring being arranged in the expansion space. The main body is fixedly arranged on an electric drill 25 through a bracket 24.

Figure 7:
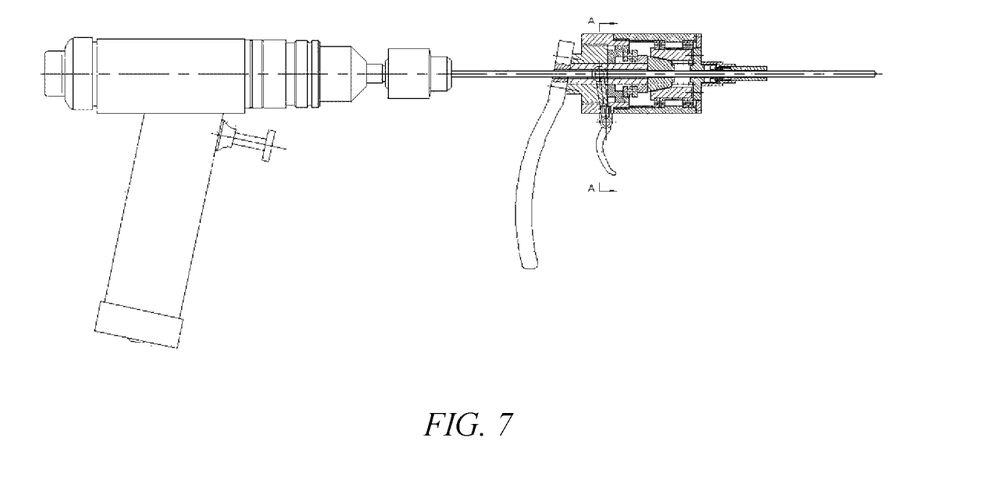
FIG. 7 is a side view of the depth limiting device of Example 3.
Figure 8:
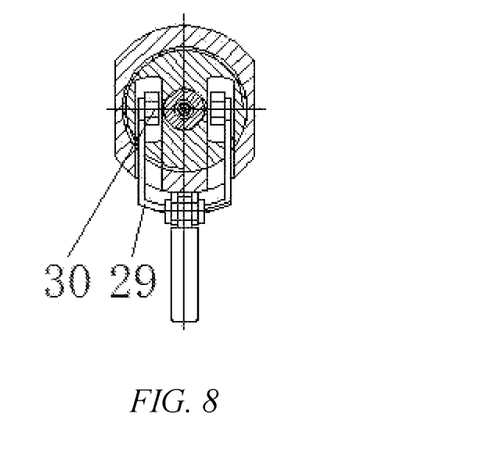
FIG. 8 is a cross-sectional view taken through A-A sectional in FIG. 6.
Figure 9:
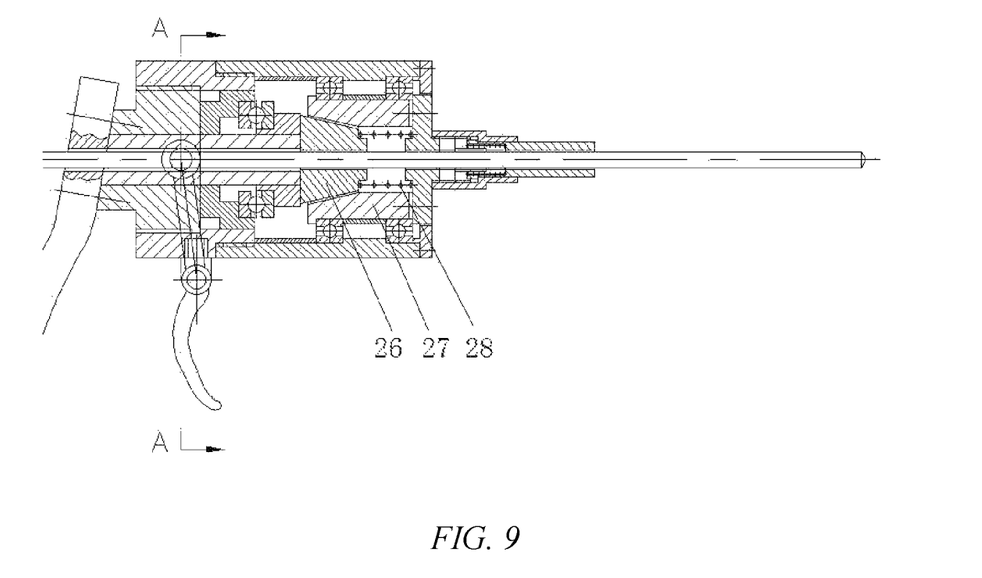
FIG. 9 is a partial enlarged drawing of FIG. 6.

Example 3: as shown in the FIGS. 7, 8, and 9, the structure which results in friction braking for the drill rod is an outer taper sleeve 26 arranged on the drill rod in a sleeving manner; an inner taper sleeve 27 is arranged outside the outer taper sleeve 26; the inner conical surface and the outer conical surface of the inner and outer taper sleeves are in a friction fit; the inner taper sleeve 27 is arranged in the main body; expansion space remains between the end face of one end of the inner taper sleeve 27 and the end face of the inner taper sleeve 27, and the end face of the one end of the inner taper sleeve 27 is located within the outer taper sleeve 26; a spring is connected between the expansion space and the main body; the structure for resulting in friction between the outer taper sleeve 26 and the drill rod includes a trigger 9; the trigger 9 is connected with the bottom of a U-shaped connecting rod 29; the two end parts of the U-shaped connecting rod 29 are respectively connected with a roller 30; and the rollers 30 drive the outer taper sleeve 26 to realize internal motion of the outer taper sleeve 26 towards the inner taper sleeve 27 along the axial line of the drill rod. The connecting sleeve 3 is arranged at the front end of the main body; and a handle 13 basically parallel with the trigger 9 is arranged at the rear end of the main body.

Figure 10:
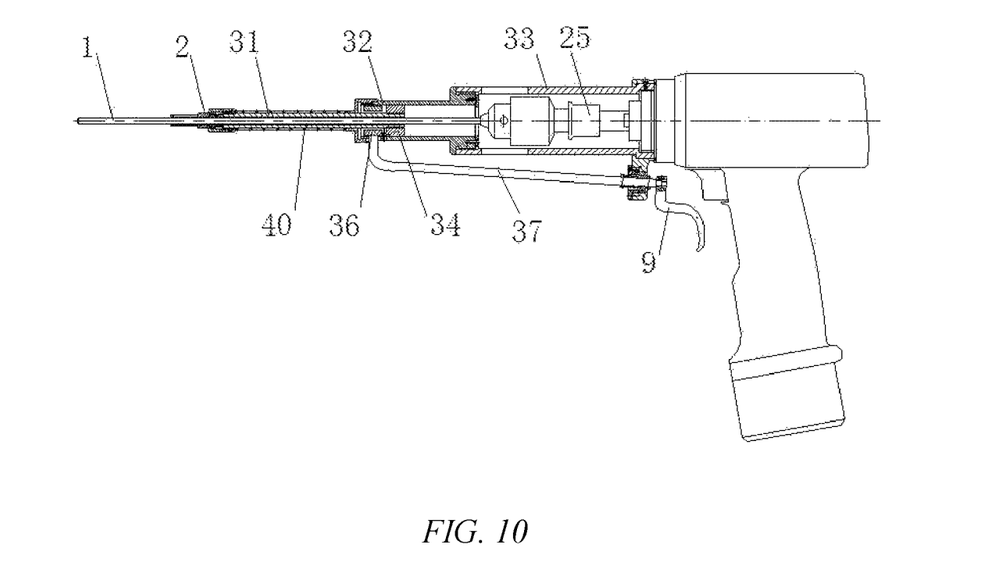
FIG. 10 is a side of the depth limiting device of Example 4.
Figure 11:
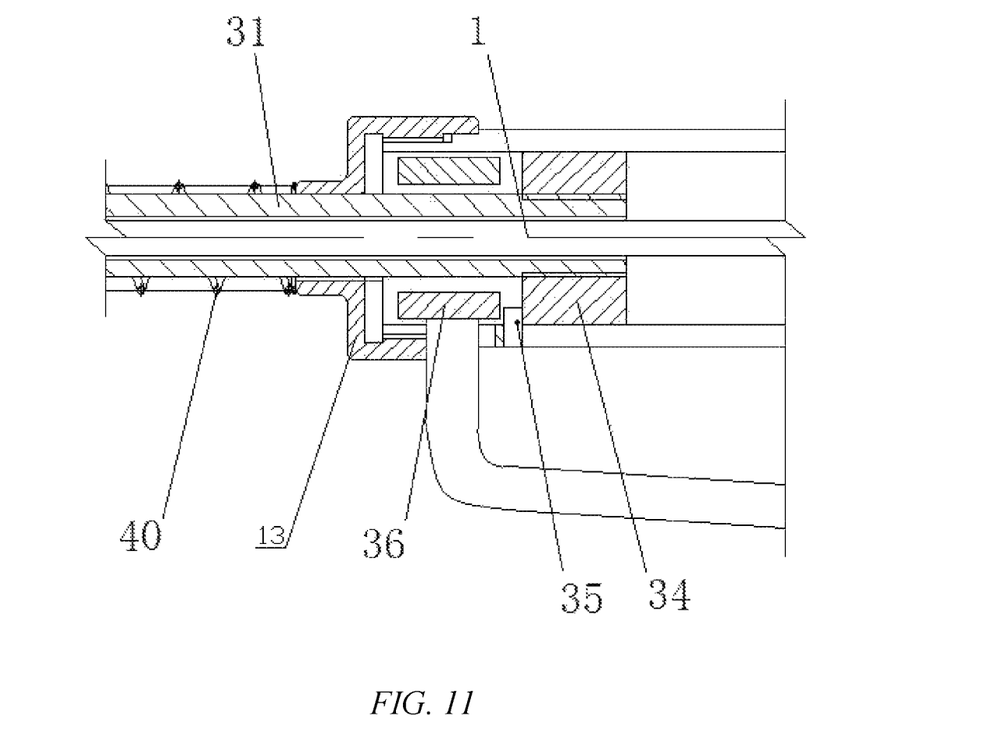
FIG. 11 is a partial enlarged drawing of FIG. 9.
Figure 14:
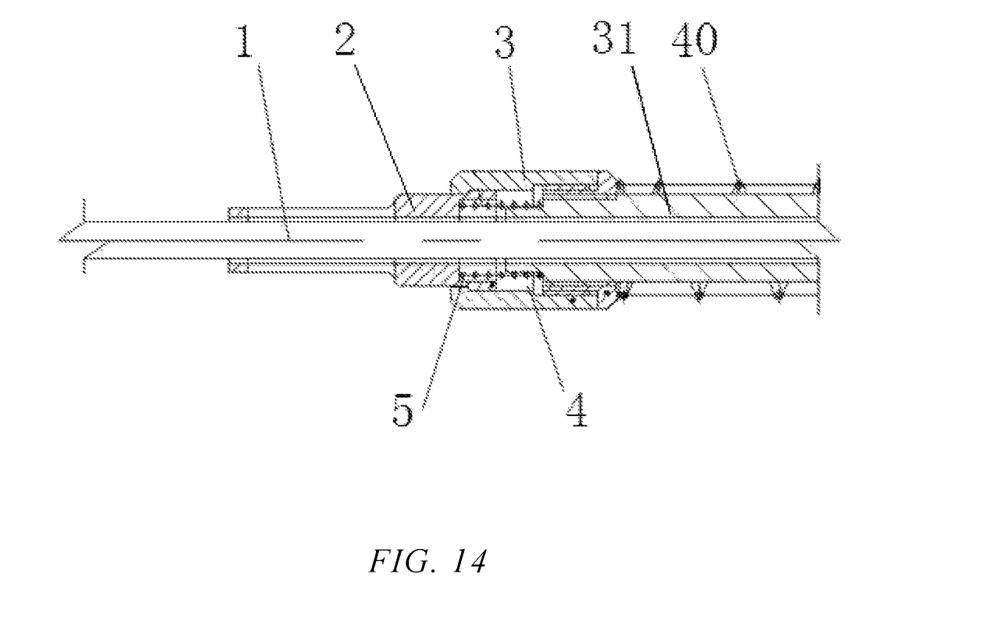
FIG. 14 shows the schematic diagram of the limited shrinking structure of Example 4 and Example 5.

Example 4: as shown in the FIGS. 10, 11 and 14, the main body includes a protective sleeve 31 at the outside of the drill rod 1, a sheath 32 at the outside of the protective sleeve 31 and a sleeve cylinder 33 fixedly arranged on the drill; the rear end of the sheath 32 is fixedly arranged at the front end of the sleeve cylinder 33; the rear end of the protective sleeve 31 is arranged in the sheath 32 and is connected with the sheath 32 in the sliding manner; the limited shrinking structure is arranged at the front end of the protective sleeve 31, that is to say, the front end of the protective sleeve 31 is the connecting sleeve 3 fixedly connected with the protective sleeve 31; the front end of the connecting sleeve 3 is the drill rod bushing 2; retraction space 4 exists between the drill rod bushing 2 and the protective sleeve 31; the first spring 5 is arranged in the retraction space 4; and a seventh spring 40 is arranged at the outside of the protective sleeve 31 and between the connecting sleeve 3 and the sheath 32.

The tail end of the protective sleeve 31 protects a guide block 34 which can slide along the inner wall of the sheath 32; the sheath 32 in front of the guide block 34 and at the back of the braking device is provided with a limiting pin 35; and the limiting pin 35 is the limiting mechanism of the guide block 34. The component which results in friction braking for the drill rod 1 is a braking ring 36; the braking ring 36 is arranged on the protective sleeve 31 in a sleeving manner and is arranged within the sheath 32; the braking ring 36 is connected with the trigger 9 through a second connecting rod 37; a gap remains respectively between the inner wall of the breaking ring and the outer wall of the protective sleeve 31 and between the outer wall of the braking ring 36 and the inner wall of the sheath 32; the wall thickness center of the braking ring 36 is coincided with the center of the gap between the protective sleeve 31 and the sheath 32; and the tail end of the second connecting rod 37 is supported at the main body.

Figure 12:
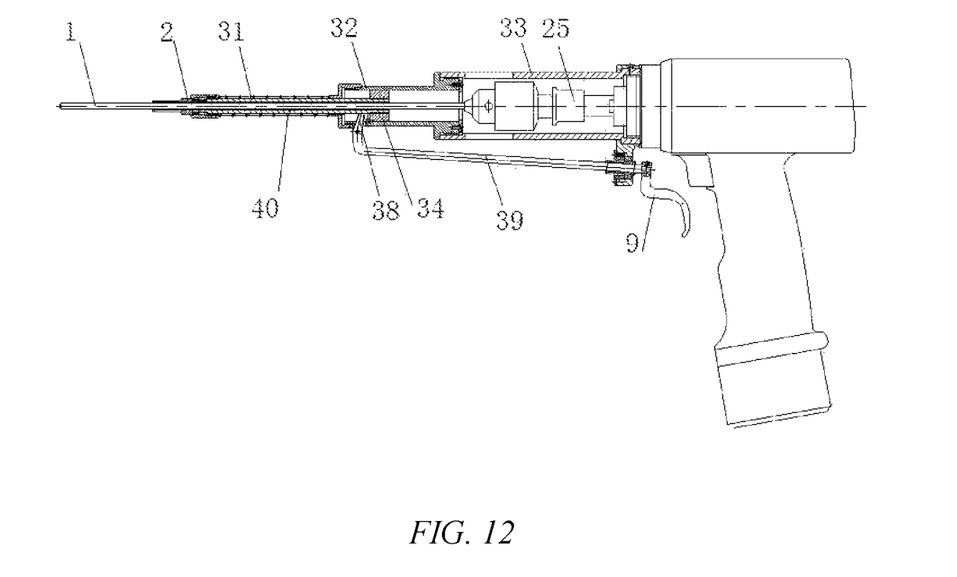
FIG. 12 is a side view of the depth limiting device of Example 5.
Figure 13:
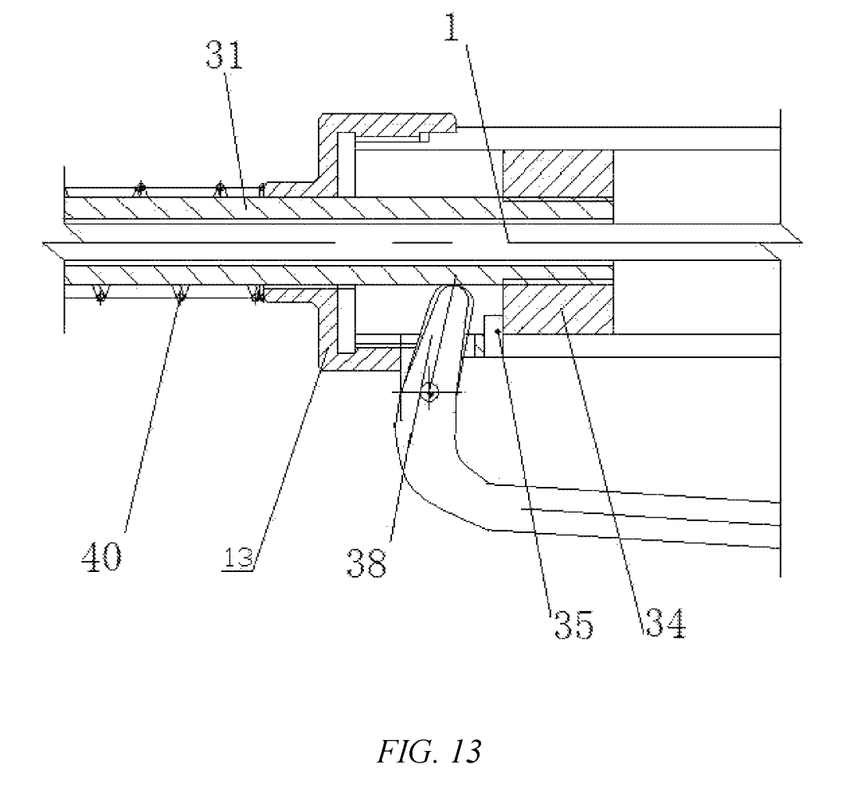
FIG. 13 is a partial enlarged drawing of FIG. 11.

Example 5: as shown in the FIGS. 12, 13 and 14, the main body includes a protective sleeve 31 at the outside of the drill rod 1, a sheath 32 at the outside of the protective sleeve 31 and a sleeve cylinder fixedly arranged on the drill; the rear end of the sheath 32 is fixedly arranged at the front end of the sleeve cylinder; the rear end of the protective sleeve 31 is arranged in the sheath 32 and is connected with the sheath 32 in the sliding manner; the limited shrinking structure is arranged at the front end of the protective sleeve 31, that is to say, the front end of the protective sleeve 31 is the connecting sleeve 3 fixedly connected with the protective sleeve 31; the front end of the connecting sleeve 3 is the drill rod bushing 2; retraction space 4 exists between the drill rod bushing 2 and the protective sleeve 31; the first spring 5 is arranged in the retraction space 4; and the seventh spring 40 is arranged at the outside of the protective sleeve 31 and between the connecting sleeve 3 and the sheath 32. The tail end of the protective sleeve 31 protects a guide block 34 which can slide along the inner wall of the sheath 32; the sheath 32 in front of the guide block 34 and at the back of the braking device is provided with a limiting pin 35; and the limiting pin 35 is the limiting mechanism of the guide block 34. The component which results in friction braking for the drill rod 1 is a second locking block 38; the second locking block 38 is rotationally arranged at the sheath 32; the second locking block 38 is provided with a steel sheet spring which is capable of restoring the second locking block 38; one end of the second locking block 38 can be supported on the periphery of the back section of the protective sleeve 31; the other end of the second locking block 38 is connected with the trigger 9 through a third connecting rod 39; and the tail end of the third connecting rod 39 is supported at the main body.

In addition, each example can be equipped with a depth measurement mechanism, and the form of the depth measurement mechanism can be obtained by one of ordinary skill in the art. The limited shrinking structure also can adopt a double-acting pneumatic cylinder structure. A buffer can be arranged at the terminal of the double-acting pneumatic cylinder structure, so that the limited shrinking structure can reduce the terminal velocity of the pneumatic cylinder steadily and prevent a stroke terminal from generating hard impact.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A depth limiting device, comprising:
    a braking structure;
    a limited shrinking structure, the limited shrinking structure including a part that surrounds a moving object and being in a home position or a compressed position; and
    a structure adapted for pushing the limited shrinking structure to the home position,
    wherein the braking structure brakes the moving object such that the moving object moves together with the depth limiting device, and
    wherein when the moving object enters into a subject, the part of the limited shrinking structure is pressed against the subject, and the limited shrinking structure moves from the home position to the compressed position and stops the moving object from entering further into the subject.

2. The depth limiting device of claim 1, wherein the moving object is a drill rod.

3. The depth limiting device of claim 1, wherein the limited shrinking structure further includes a connecting rod and a connecting sleeve; the connecting sleeve internally includes a retraction space, and the structure adapted for pushing the limited shrinking structure to the home position is arranged in the retraction space.

4. The depth limiting device of claim 3, wherein the structure adapted for pushing the limited shrinking structure to the home position is a spring.

5. The depth limiting device of claim 1, wherein the braking structure is an axial braking structure and a friction braking structure.

* * * * *